United States Patent [19]
Cavicchi et al.

[11] Patent Number: 6,079,873
[45] Date of Patent: Jun. 27, 2000

[54] MICRON-SCALE DIFFERENTIAL SCANNING CALORIMETER ON A CHIP

[75] Inventors: Richard E. Cavicchi, Washington Grove; Gregory Ernest Poirier, Potomac; John S. Suehle, Westminster; Michael Gaitan, Potomac, all of Md.; Nim H. Tea, Skokie, Ill.

[73] Assignee: The United States of America as represented by the Secretary of Commerce, Washington, D.C.

[21] Appl. No.: 09/107,064

[22] Filed: Jun. 30, 1998

Related U.S. Application Data

[60] Provisional application No. 60/063,192, Oct. 20, 1997.

[51] Int. Cl.[7] .................................................. G01N 25/00
[52] U.S. Cl. .......................... 374/10; 374/31; 374/12; 422/51; 422/95
[58] Field of Search .......................... 374/10, 12, 13, 374/31, 132, 133, 29, 30; 422/51, 95

[56] References Cited

U.S. PATENT DOCUMENTS

| | | | |
|---|---|---|---|
| 3,798,003 | 3/1974 | Ensley et al. . | |
| 4,255,961 | 3/1981 | Biltonen et al. | 73/15.002 |
| 4,416,551 | 11/1983 | Kim . | |
| 4,677,416 | 6/1987 | Nishimoto et al. | 338/35 |
| 5,287,081 | 2/1994 | Kinard et al. | 338/24 |
| 5,451,371 | 9/1995 | Zanini-Fisher et al. . | |
| 5,549,387 | 8/1996 | Shawe et al. | 374/10 |
| 5,599,104 | 2/1997 | Nakamura et al. . | |
| 5,652,443 | 7/1997 | Kasai | 257/252 |
| 5,813,764 | 9/1998 | Visser et al. | 374/12 |
| 5,842,788 | 12/1998 | Danley et al. | 374/12 |
| 5,902,556 | 5/1999 | Van De Vyver et al. | 422/174 |

FOREIGN PATENT DOCUMENTS

| | | | |
|---|---|---|---|
| 0129228 | 8/1983 | Japan | 374/30 |

OTHER PUBLICATIONS

Denlinger et al., "Thin film microcalorimeter for heat capacity measurements," *REv. Sci. Instrum.* vol. 65, No. 4, Apr. 1994, pp. 946–957.

*Primary Examiner*—Diego Gutierrez
*Assistant Examiner*—Lydia De Jesús
*Attorney, Agent, or Firm*—Charles E. Rohrer

[57] ABSTRACT

A differential scanning microcalorimeter produced on a silicon chip enables microscopic scanning calorimetry measurements of small samples and thin films. The chip may be fabricated using standard CMOS processes. The microcalorimeter includes a reference zone and a sample zone. The reference and sample zones may be at opposite ends of a suspended platform or may reside on separate platforms. An integrated polysilicon heater provides heat to each zone. A thermopile consisting of a succession of thermocouple junctions generates a voltage representing the temperature difference between the reference and sample zones. Temperature differences between the zones provide information about the chemical reactions and phase transitions that occur in a sample placed in the sample zone.

20 Claims, 5 Drawing Sheets

MICRON-SCALE DIFFERENTIAL SCANNING CALORIMETER ON A CHIP

This application claims the benefit of U.S. Provisional Patent Application Ser. No. 60/063,192, filed Oct. 20, 1997.

TECHNICAL FIELD

The invention relates to calorimetry, particularly to differential scanning microcalorimeters.

BACKGROUND OF THE INVENTION

Calorimetry is a measurement technique used to measure the changes in heat of an isolated system. Differential scanning calorimetry applies an approximately linear temperature profile to an isolated system while a reaction occurs in one part of the system. Differences in temperature across the temperature scan provide information about the thermodynamics of the reaction. Microcalorimetry is a measurement technique based upon a small sized calorimeter and as a result is applicable to analyzing the reactions of small samples, for example, thin films. A microcalorimeter is able to measure the heat of reactions of thin films because of the small size of the instrument; in ordinary calorimeter ovens, the thin film is too insignificant in the device to gain any information about its chemical reaction.

A non-scanning, that is, constant temperature microcalorimeter device is described in U.S. Pat. No. 5,451,371. The device is built on a silicon base and the base is etched, leaving a frame of silicon supporting two suspended polysilicon platforms. A catalyst is used on one platform to sense the presence of hydrocarbons. Platinum resistors on each platform serve as heaters and thermometers.

An article entitled "Thin Film Microcalorimeter for Heat Capacity Measurements from 1.5 to 800 K", Denlinger et al., Review of Scientific Instruments, American Institute of Physics, 1994, describes a microcalorimeter fabricated from a silicon nitride membrane mounted in a silicon frame. The membrane provides a platform that contains a platinum heater, a thin film platinum thermometer for high temperatures, and a Nb—Si low-temperature thermometer. The device does not have separate sample and reference zones for accurate scanning measurements.

The prior art fails to adequately resolve issues of thermal isolation and measurement accuracy in scanning microcalorimeters. It is an object of this invention to provide a scanning microcalorimeter on a chip with good thermal isolation between sample and reference zones to enable the measurement of small samples and thin films or monolayer films over a large range of temperatures.

SUMMARY OF THE INVENTION

The invention is a micron-scale differential scanning calorimeter produced on a silicon or gallium arsenide chip that allows for microscopic differential scanning calorimetry measurements of small samples. In several embodiments, the microcalorimeter includes a reference zone and a sample zone, each with an integrated polysilicon heater and a thermopile. In one embodiment, the reference and sample zones are on separate suspended platforms. In other embodiments, the reference and sample zones are at opposite ends of a single suspended platform. With a chip produced from silicon substrate, the thermopile consists of multiple polysilicon/aluminum junctions that are connected in series and that alternate between the reference and sample zones. The thermopile voltage provides a measure of the temperature difference between the two zones and helps cancel the effects of common-mode thermal variations in the surrounding environment. In one embodiment, a single heater provides heat to the sample and reference zones. In another embodiment, the heater comprises an oven that contains the reference and sample zones, in which case the microcalorimeter may be designed without an integrated heater.

In performing a differential scanning calorimetry measurement according to the invention, the reference and sample zones are heated simultaneously with a ramped temperature profile. The electrical power profiles to the heaters may be calibrated such that the output voltage of the thermopile is zero in the absence of any differences in the thermal processes occurring in the two zones. A sample material or a sensing material may then be applied to the sample zone. As the temperature is scanned, a loss or gain of heat associated with a reaction or phase transition in the sample zone results in the production of a difference signal by the thermopile. Mapping the difference over a range of temperature provides information about the reaction. Types of sensing materials include a catalyst for chemical sensing, a material that exhibits a phase transition, and a chemically selective reactive material.

DETAILED DESCRIPTION

Figure 1:
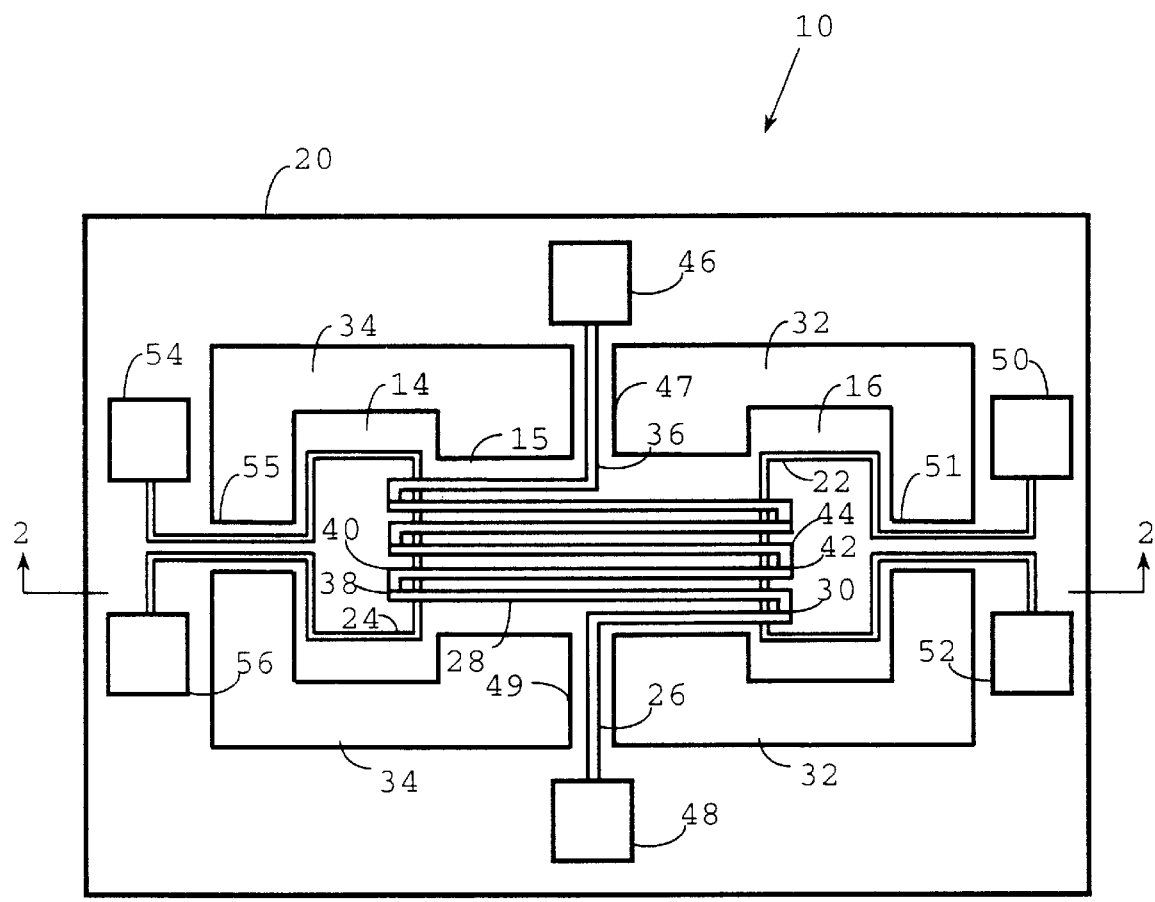
FIG. 1 is a schematic block diagram of a first embodiment of the microcalorimeter of the invention.
Figure 2:
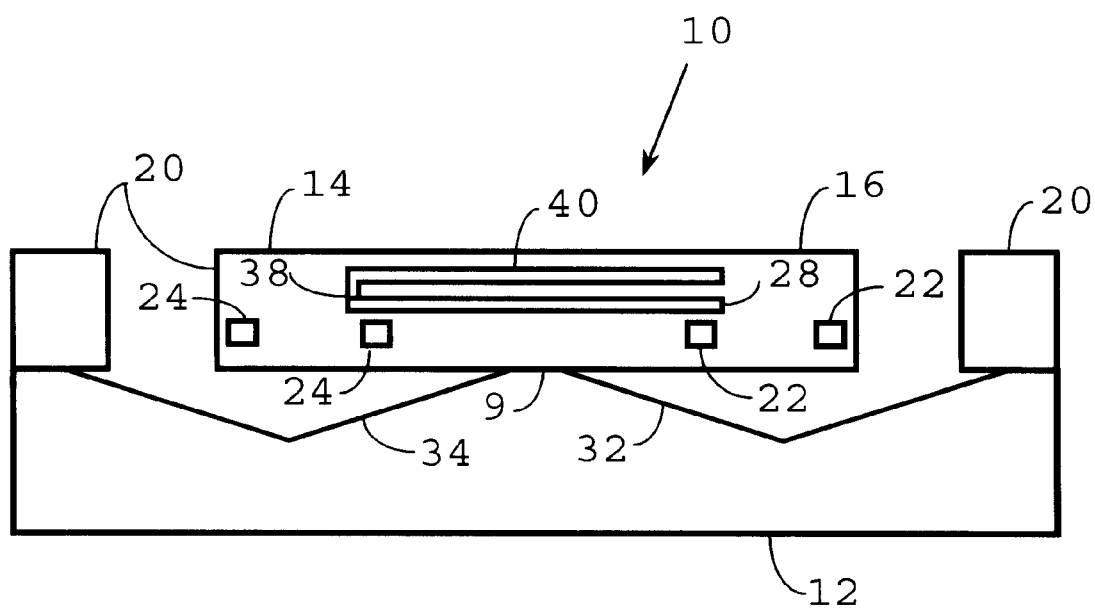
FIG. 2 is a cross-sectional elevation view of the microcalorimeter taken along line 2—2 of FIG. 1.

FIG. 1 is a plan view of a microcalorimeter 10 of the present invention comprising a dielectric such as silicon oxide layer 20 attached to one side of a substrate such as silicon substrate 12 thereby forming a single chip. Silicon substrate 12 is not visible in FIG. 1 but is shown in FIG. 2. A suspended reference platform 14 and a suspended sample platform 16 are located within the boundaries of the silicon oxide layer 20. The reference platform 14 and the sample platform 16 are silicon oxide platforms with layers of polysilicon and aluminum embedded therein. The platforms 14 and 16 are suspended over pits 34 and 32, respectively, which are etched into the silicon substrate. The pits 34 and 32 in the bulk silicon are visible in FIG. 1 through openings in the silicon oxide layer 20 that forms the platforms 14 and 16. The platforms 14 and 16 are held in place by four silicon oxide arms 47, 49, 51 and 55 extending from the perimeter of the silicon oxide layer 20. Arms 51 and 55 form bridges over the pits from the platforms to the chip periphery where connecting wirebond pads are located for heaters 22 and 24. A thermopile 15 is buried within layer 20 and crosses between the platforms 14 and 16. A ridge 9 of bulk silicon is present under silicon oxide arms 47 and 49 thereby separating the pits 34 and 32. Ridge 9 is shown in FIG. 2.

To illustrate the size of the instrument in an actual prototype, platforms 14 and 16 are each about 50 microns in the vertical dimension and about 35 microns in the horizontal dimension.

Polysilicon heaters 22 and 24 are buried within the silicon oxide layer 20. The polysilicon heater 22 extends over the arm 51 which bridges across pit 32 to sample platform 16. The intermediate portion of the heater 22 is located in the sample platform 16. Heater 22 is provided with two wirebond terminal pads 50 and 52. The polysilicon heater 24 follows a path across the supporting arm 55 over pit 34, and the intermediate portion of the heater 24 is located in the reference platform 14. The heater 24 forms a complete circuit between two wirebond terminals 54 and 56.

The thermopile 15 is comprised of metals forming thermocouple junctions. In FIG. 1, an aluminum line 26 leads into the structure from a wirebond pad 48 and an aluminum line 36 leads out of the structure to a wirebond pad 46. The aluminum line 26 makes a junction 30 with a polysilicon line 28 on the sample platform 16. The polysilicon line 28 leads to the reference platform 14 where it makes a junction 38 with another aluminum line 40. The aluminum line 40 returns to the sample platform 16 and makes a junction 42 with a polysilicon line 44. This series of polysilicon-aluminum junctions is repeated N times, producing a thermopile voltage $V=NV_{\Delta T}$, where $V_{\Delta T}$ is the voltage produced by a temperature difference $\Delta T$ at one of the thermocouples. A larger number N of junctions results in a greater thermopile voltage V. However, a larger number of junctions also results in a larger number of lines running between the platforms 14 and 16, thus causing additional thermal coupling between the platforms 14 and 16. The microcalorimeter 10 measures the difference in temperature between the platforms 14 and 16. However, since thermal coupling between the platforms 14 and 16 reduces the accuracy of the measurement, it is preferable to weigh the benefit of increasing the thermopile voltage V with the cost associated with reducing the thermal isolation between the platforms 14 and 16.

The use of a thermopile enables a wide operational temperature range that is potentially greater than 500° C. This wide temperature range is an important advance for applications pertaining to chemical detection and recognition based on catalytic reactions. Another advantage of the thermopile 15 is that it is able to null the effects of temperature drift in the surrounding environment and thereby enhance the thermal isolation of the device. Thus, an important aspect of the microcalorimeter 10 is that the reference and sample areas 14 and 16 are close together and thereby encounter the same environment. The thermopile 15 also enables a new sensing principle for microcalorimeters based on the detection of voltage changes due to thermal chances in the sample zone.

To calibrate the device over a desired temperature range, power is applied to heater 22 in a first step to create a temperature rise at sample zone 16 of a desired number of degrees. A similar amount of power is applied to heater 24 to create a temperature rise at the reference zone 14. If the two zones are heated to the same temperature, the output of thermopile 15 is zero. If not, power is adjusted to achieve an approximately zero thermopile output. If digital to analog (DAC) converters are used to drive the heaters, a perfect null may not be possible. If a perfect null is not achieved, the unbalance signal is stored and subtracted during subsequent measurement operations. The power sources are not shown in FIG. 1 but it is obvious that the reference zone power source is connected to wirebond pads 54 and 56 while the sample zone power source is connected to wirebond pads 50 and 52. Thermopile voltage to be measured appears across wirebond pads 46 and 48.

The calibration is continued over the entire temperature range in successive steps, recording the power to each zone at each step thereby producing a power profile that provides a null (or approximately null) thermopile output voltage over the entire temperature range.

After calibration, a substance to be evaluated is placed in the sample zone. The temperature of the microcalorimeter is then changed in successive steps according to the power profile with thermopile output voltages recorded at each step. Any variation from the null is due to the reaction of the substance under test to the change in temperature.

FIG. 2 illustrates a slice of the microcalorimeter 10 in a cross-sectional elevation view taken horizontally across the chip through thermocouple junction 38 along line 2—2 of FIG. 1. The silicon substrate 12 provides a base for the layer of silicon oxide 20. Layers of polysilicon embedded in silicon oxide 20 form the polysilicon heaters 22 and 24. The thermopile 15 is embedded in silicon oxide 20 and comprised of layers of polysilicon and aluminum from which lines (such as the lines 28 and 40, respectively) are formed. Contacts between layers of polysilicon and aluminum form thermocouple junctions, such as junction 38. The silicon oxide electrically insulates this layers of polysilicon 22, 24, and 28 and the aluminum layers 40 from each other. Openings in the silicon oxide layer 20 provide access to the silicon substrate 12 for surface etching of the pits 32 and 34. FIG. 2 shows the platform 14 suspended over pit 34 and platform 16 suspended over pit 32. The pits are separated by ridge 9.

The microcalorimeter chip is produced using a conventional complementary metal oxide semiconductor (CMOS) process in which the layout of the silicon oxide, polysilicon, and aluminum layers is specified. The layout is used to form a mask. The conventional CMOS process determines the thickness, exact composition, resistivity, and spatial resolution of the layers in the fabricated chip. The CMOS process may be used to fabricate a microcalorimeter chip from other types of substrate materials such as gallium arsenide coupled with appropriate dielectrics and thermocouple metals. The CMOS process may also be used to fabricate amplifying and switching devices (not shown) that can be integrated into the microcalorimeter.

The silicon substrate 12 is surface etched using xenon difluoride or ethylene diamine pyrochatechol water to form the pits 32 and 34 underneath the reference and sample zones 14 and 16. The pits 32 and 34 help to thermally isolate the reference and sample zones 14 and 16 from the silicon substrate 12. In that manner, thermal isolation is improved to reduce heat loss to the substrate 12, thereby enhancing the sensitivity of the microcalorimeter 10 and reducing the power required to operate the polysilicon heaters 22 and 24.

A sample material (not shown) or a sensing material (not shown) may be deposited on the sample platform 16. Heat changes due to chemical reactions or physical changes on the sample platform 16 are measured with respect to the reference platform 14. Many different sensing materials may be used. For example, an absorbent material may be placed on the sample platform 16 to detect gaseous reactions. As the platforms 14 and 16 are heated, the absorbent material releases the gas, thereby providing a measurable reaction. Also, catalytic metals such as Pd, Pt, Rh, and Ni can be used on sample area 16 to generate a thermal response to hydrocarbons. High surface-area layers of reactant materials that produce heat when a specific analyte is present can be applied to the sample area 16 to enhance the sensitivity of the calorimeter 10 for those specific analytes.

As described above, the microcalorimeter 10 is preferably operated in a ramped temperature mode. The polysilicon heaters 22 and 24 are calibrated so that the amount of electrical energy needed to provide a specific number of degrees of additional heat to each platform 14 and 16 is known over the entire temperature range being measured. In that manner, a power profile for the heaters 22 and 24 is obtained so that a null profile voltage is maintained by the thermopile 15 over the entire temperature range. With an analyte present on the sample platform 16, the same heater power schedule is used and the temperature difference is monitored. As the two platforms 14 and 16 are heated in an identical manner, any temperature differences between the platforms 14 and 16 are sensed by the production of a thermopile voltage. Such temperatures differences are due to a chemical reaction or physical change occurring on the sample platform 16. Measurements of the thermopile voltages provide the temperature differences between the platforms 14 and 16 and provides information relating to the chemical reaction or physical change occurring on the sample platform 16. Alternative temperature operation, such as customized scans (including temperature steps and pulses), may be used to enhance the detection of chemical species.

Figure 3:
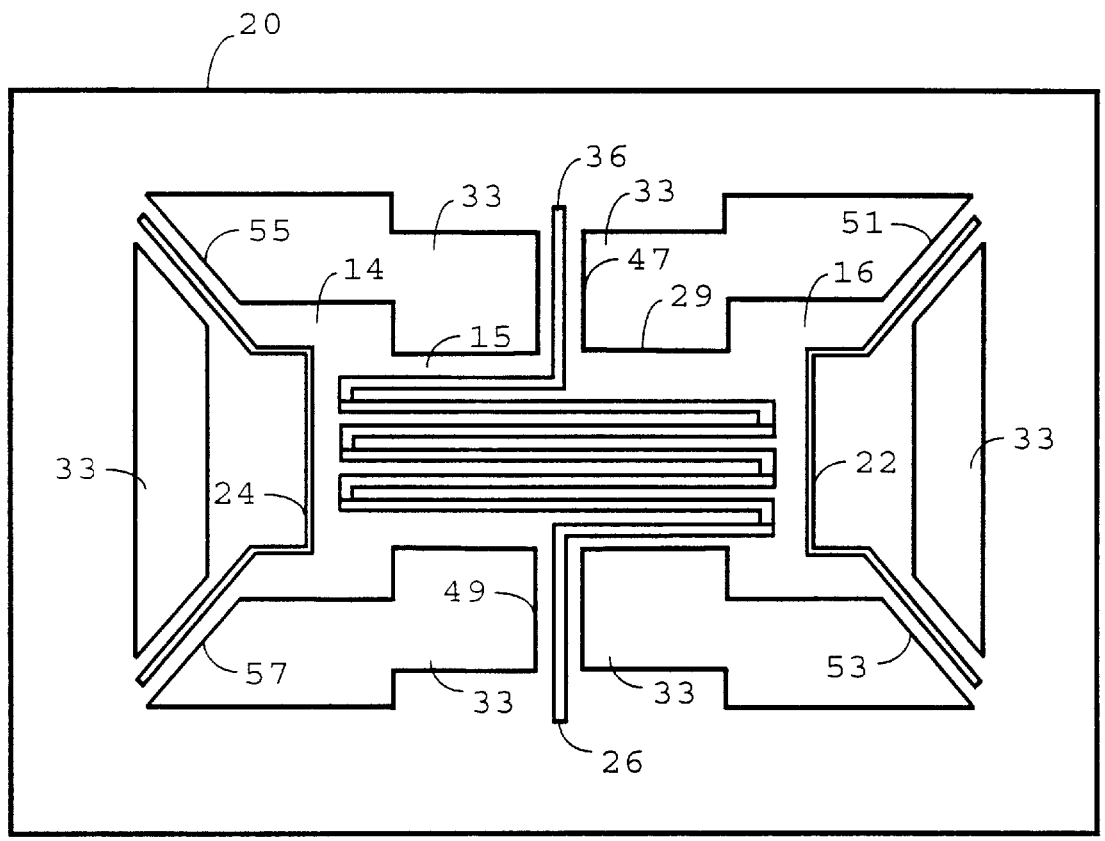
FIG. 3 is a schematic block diagram of a second embodiment of the microcalorimeter of the invention in which a single suspended platform has reference and sample zones.

FIG. 3 shows a differential scanning calorimeter similar to the microcalorimeter shown in FIG. 1 except that it has a single platform 29 suspended over a single pit 33 in order to enhance thermal isolation of the zones from the substrate. Reference and sample zones 14 and 16 are at opposite ends of the platform 29. Neither thermopile lines 26 and 36 nor heaters 22 and 24 are shown connecting to wirebond pads (not shown). However, it is understood that connections to wirebond pads similar to those shown in FIG. 1 may be included. If desired, the microcalorimeter shown in FIG. 3 may be designed without built-in heaters 22 and 24. In that event, a conventional oven (not shown) would be used to heat the microcalorimeter. An array of such microcalorimeters inside an oven (not shown) would be useful for DNA diagnostics. For example, each array element's sample zone 16 may be coated with a different selective coating for a specific DNA sequence. Hybridization on selected array elements can be observed via calorimetric difference signals when the array is heated through the characteristic temperature for DNA hybridizing.

Figure 4:
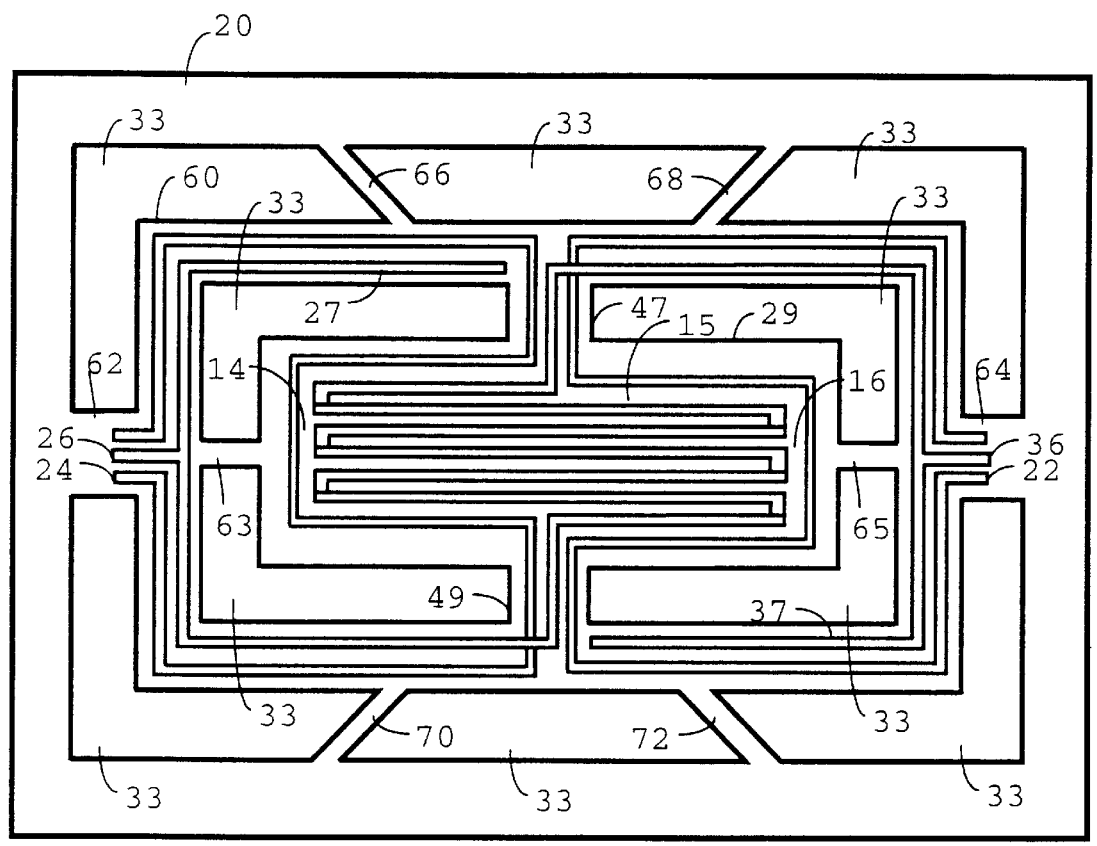
FIG. 4 is a schematic block diagram of a third embodiment of the microcalorimeter of the invention that includes a dual concentric suspended structure.

An alternate embodiment of a microcalorimeter design shown in FIG. 4 includes a similar arrangement of components as described in FIG. 3 with one pit 33 underlying platform 29 with reference zone 14 and sample zone 16 at opposite ends of platform 29. The microcalorimeter design shown in FIG. 4 includes a suspended bridge 60 that provides additional thermal isolation for platform 29 from its surroundings. The suspended bridge 60 is suspended over pit 33 by six supporting arms 62, 64, 66, 68, 70, and 72. Four supporting arms 47, 49, 63, and 65 extend from the suspended bridge 60 to the platform 29. Like the microcalorimeter shown in FIG. 3, reference and sample zones 14 and 16 are at opposite ends of the platform 29. Heater line 22 begins and ends on supporting arm 64. The heater line 22 traverses the suspended bridge 60 and crosses arm 47 to enter the platform 29. The intermediate part of the heater line 22 passes through the sample area 16 and returns to the suspended bridge 60 via supporting arm 49. Heater line 24 begins and ends on supporting arm 62. The heater line 24 traverses bridge 60 and is connected to the platform 29 via supporting arms 47 and 49. The intermediate part of the heater 24 provides heat to the reference zone 14. Thermopile connecting line 36 begins at supporting arm 64 and enters the suspended bridge 60. The thermopile connecting line 36 traverses the suspended bridge 60, crosses over the heater line 22, and enters supporting arm 47 where it turns and enters the platform 29. The thermopile connecting line 36 then becomes part of the thermopile 15. The thermopile 15 is connected to thermopile connecting line 26 on the platform 29. Thermopile connecting line 26 crosses the supporting arm 49 to the suspended bridge 60 and then crosses over the heater line 24 to terminate at supporting arm 62. A branch line 27 connected to thermopile connecting line 26 traverses the suspended bridge 60 and terminates near the supporting arm 47. Likewise, a branch line 37 connected to the thermopile connecting line 36 near the supporting arm 64 traverses the suspended bridge 60 and terminates just before the supporting arm 49. The purpose of the branch lines 27 and 37 is to provide thermal balance to the suspended bridge 60 with respect to the lines 26 and 36. Although not shown, wirebond pads similar to those shown in FIG. 1 may be connected to the ends of the heaters 22 and 24 and the thermopile lines 26 and 36.

Figure 5:
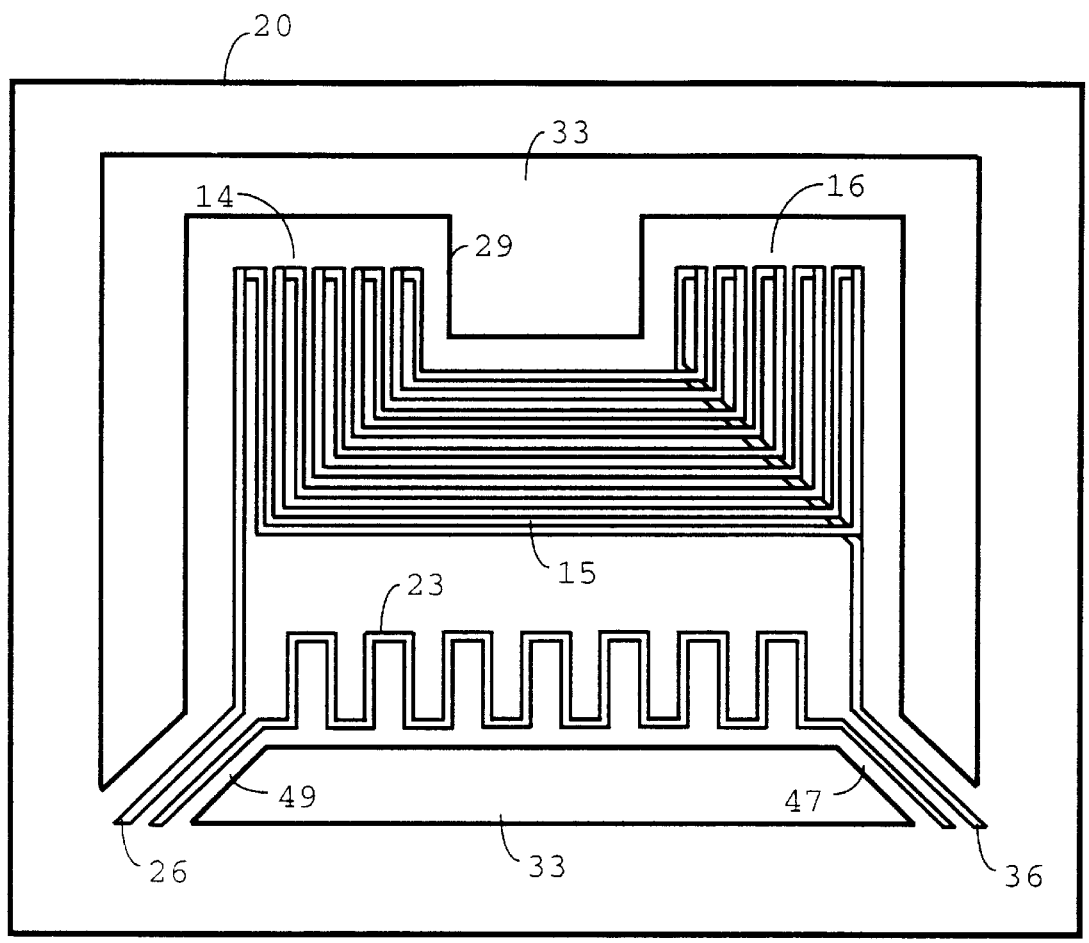
FIG. 5 is a schematic block diagram of a fourth embodiment of the microcalorimeter of the invention that shows a single heater.

An alternate embodiment of this invention is illustrated in FIG. 5. In this alternate embodiment, suspended platform 29 is held by supporting arms 47 and 49, and a single heater 23 heats both reference and sample zones 14 and 16 of the suspended platform 29. The arrangement of thermopile 15 has thermocouple junctions located at the reference and sample zones. Wirebond pads (not shown) may be connected to the ends of the heater lines 23 and thermopile lines 26 and 36. Since only one heater is used in this embodiment, calibration of the instrument over a temperature range may indicate some non-null voltages (unbalance signals) in the thermopile at various temperatures. Knowledge of the thermopile voltage valuation over the temperature range is then used as the base profile for subsequent measurements of samples. Such unbalance signals are subtracted from the subsequent measurements.

While the description above refers to particular embodiments of the present invention, it will be understood that many modifications may be made without departing from the spirit thereof. The accompanying claims are intended to cover such modifications as would fall within the scope and spirit of the present invention.

What is claimed is:

1. A micron-scale calorimeter on a single chip for providing microscopic calorimetry measurements of small samples, the microcalorimeter comprising:

a substrate for said chip, a reference zone and a separate sample zone, the zones located on at least one suspended platform, said platform suspended over at least one pit etched into said substrate, said zones positioned close to each other to minimize temperature drift in the environment, said zones being thermally isolated from each other;

at least one heater for uniformly heating said zones; and a single thermopile comprising a plurality of thermocouple junctions, a first set of said plurality of junctions being integrated into said reference zone and a second set of said plurality of junctions being integrated into said sample zone.

2. The microcalorimeter of claim 1 wherein said reference zone is located on a first suspended platform and said sample zone is located on a second suspended platform, said thermopile crossing from said first set of junctions on said first suspended platform to said second set of junctions on said second suspended platform.

3. The microcalorimeter of claim 1 wherein said reference zone is located on one end of said suspended platform and said sample zone is located at the opposite end of said suspended platform, said thermopile crossing said suspended platform from said first set of junctions to said second set of junctions.

4. The microcalorimeter of claim 1 wherein said heater is comprised of a first heating element to heat said reference zone and a second heating element to heat said sample zone, each said heating element separately supplied with power.

5. The microcalorimeter of claim 4 wherein said microcalorimeter is calibrated over a temperature range to produce a power profile, said calibration performed by heating said zones a specified number of degrees in a plurality of successive steps across said temperature range and adjusting power supplied to at least one of said zones at each step so that said thermopile produces approximately a null voltage output at each step across the entire temperature range.

6. The microcalorimeter of claim 5 wherein a substance to be evaluated is located in said sample zone, said microcalorimeter scanned over at least a portion of said temperature range according to said power profile, said thermopile producing a differential voltage between said reference zone and said sample zone at each step, said differential voltage being the result of the presence of said substance.

7. The microcalorimeter of claim 6 wherein said substance is a thin film.

8. The microcalorimeter of claim 1 wherein said chip is produced with a standard CMOS process.

9. The microcalorimeter of claim 8 wherein said substrate is silicon and further including a layer of dielectric material, and conductors for said plurality of thermocouple junctions, said at least one pit etched into said substrate.

10. The microcalorimeter of claim 9 wherein the layer of dielectric material is silicon dioxide and the conductors are polysilicon and aluminum.

11. The microcalorimeter of claim 8 wherein said substrate is gallium arsenide and further including a layer of dielectric material, and metals for said plurality of thermocouple junctions, said at least one pit etched into said substrate.

12. The microcalorimeter of claim 1 wherein said heater is comprised of a single heating element and wherein said microcalorimeter is calibrated over a temperature range to produce a thermopile voltage profile over said temperature range, said calibration performed by heating said zones a specified number of degrees in a plurality of successive steps across said temperature range.

13. The microcalorimeter of claim 12 wherein a substance to be evaluated is located in said sample zone, said microcalorimeter scanned across at least a portion of said temperature range, said thermopile producing a voltage between said reference zone and said sample zone at each step, the difference between the produced voltage and said thermopile voltage profile at each step being the result of the presence of said substance.

14. The microcalorimeter of claim 1 wherein said heater is an oven that encloses said zones.

15. The microcalorimeter of claim 14 wherein said microcalorimeter is calibrated over a temperature range to produce a thermopile voltage profile over said temperature range, said calibration performed by heating said zones a specified number of degrees in a plurality of successive steps across said temperature range.

16. The microcalorimeter of claim 15 wherein a substance to be evaluated is located in said sample zone, said microcalorimeter scanned across at least a portion of said temperature range, said thermopile producing a voltage between said reference zone and said sample zone at each step, the difference between the produced voltage and said thermopile voltage profile at each step being the result of the presence of said substance.

17. The microcalorimeter of claim 14 wherein said chip is produced with a standard CMOS process.

18. The microcalorimeter of claim 17 wherein said substrate is silicon and further including a layer of dielectric material, and conductors for said plurality of thermocouple junctions, said at least one pit etched into said substrate.

19. The microcalorimeter of claim 17 wherein said substrate is gallium arsenide and further including a layer of dielectric material, and metals for said plurality of thermocouple junctions, said at least one pit etched into said substrate.

20. The microcalorimeter of claim 18 wherein the layer of dielectric material is silicon dioxide and the conductors are polysilicon and aluminum.

* * * * *